United States Patent
Donini et al.

(10) Patent No.: US 11,771,757 B2
(45) Date of Patent: ***Oct. 3, 2023

(54) COMPOSITIONS AND METHODS OF MANUFACTURING TRIVALENT FILOVIRUS VACCINES

(71) Applicants: Soligenix, Inc., Princeton, NJ (US); University of Hawaii, Honolulu, HI (US)

(72) Inventors: Oreola Donini, Coquitlam (CA); Axel Lehrer, Honolulu, HI (US)

(73) Assignees: Soligenix, Inc., Princeton, NJ (US); University of Hawaii, Honolulu, HI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/902,662

(22) Filed: Sep. 2, 2022

(65) Prior Publication Data
US 2023/0093418 A1    Mar. 23, 2023

Related U.S. Application Data

(63) Continuation of application No. 16/879,668, filed on May 20, 2020, now Pat. No. 11,433,129.
(Continued)

(51) Int. Cl.
*A61K 39/12* (2006.01)
*C12N 7/00* (2006.01)
(Continued)

(52) U.S. Cl.
CPC .............. *A61K 39/12* (2013.01); *A61K 39/39* (2013.01); *A61P 31/14* (2018.01); *C12N 7/00* (2013.01);
(Continued)

(58) Field of Classification Search
None
See application file for complete search history.

(56) References Cited

U.S. PATENT DOCUMENTS

| 6,013,264 | A | 1/2000 | Petre et al. |
| 8,753,646 | B2 | 6/2014 | Abe et al. |

(Continued)

FOREIGN PATENT DOCUMENTS

| WO | 1997000697 | 1/1997 |
| WO | 1998000167 | 1/1998 |

(Continued)

OTHER PUBLICATIONS

Iyer et al. (Journal of Pharmaceutical Sciences. Mar. 2017; 106: 1490-1498).*

(Continued)

*Primary Examiner* — Shanon A. Foley
(74) *Attorney, Agent, or Firm* — Lewis Kohn & Walker LLP; David M. Kohn

(57) ABSTRACT

Disclosed is a stable immunogenic composition capable of eliciting a robust and durable immune response, comprising at least one antigen consisting of a filovirus glycoprotein and at least one nano-emulsion adjuvant which are co-lyophilized and can be reconstituted immediately prior to use. Also disclosed is a vaccine composition comprising at least two antigens, wherein each antigen is specific to a different genus of filovirus and which also comprises at least one nano-emulsion adjuvant.

8 Claims, 14 Drawing Sheets

Related U.S. Application Data

(60) Provisional application No. 62/850,443, filed on May 20, 2019.

(51) Int. Cl.
    *A61K 39/39*     (2006.01)
    *A61P 31/14*     (2006.01)
    *A61K 39/00*     (2006.01)

(52) U.S. Cl.
    CPC ............ *A61K 2039/55566* (2013.01); *A61K 2039/575* (2013.01); *A61K 2039/70* (2013.01)

(56) References Cited

U.S. PATENT DOCUMENTS

| | | | |
|---|---|---|---|
| 11,433,129 B2 * | 9/2022 | Donini | .................... A61P 31/14 |
| 2009/0291095 A1 * | 11/2009 | Baker, Jr. | ............... A61K 39/07 |
| | | | 424/184.1 |
| 2012/0136142 A1 | 5/2012 | Kumar et al. | |

FOREIGN PATENT DOCUMENTS

| | | |
|---|---|---|
| WO | 2002000249 | 1/2002 |
| WO | 2006097851 | 9/2006 |
| WO | 2007054820 | 5/2007 |
| WO | 2019051098 | 3/2019 |

OTHER PUBLICATIONS

Mok et al. (The Open Virology Journal. 2012; 6: 12-22).*
Preston et al. (Vaccine. 2021; 5650-5657).*
Extended European Search Report for correspondence European Patent Application No. 20810813.4 dated May 23, 2023.
Lehrer et al. "Recombinant proteins of Zaire ebolavirus induce potent humoral and cellular immune responses and protect against live infection in mice." (2017) 36(22):3090-3100.
Lehrer et al. "Development of Thermostable Filovirus Vaccines Based on Recombinant Insect Cell Expressed Subunits." (2018) Retrieved from Internet: URL:https://www.astmh.org/ASTMH/media/Documents/2018-Abstract-Book-FINAL-11-13.pdf.
Reynolds et al. "Ebola and Marburg virus vaccines." (2017) Virus Genes 53:501-515.
Gross et al. "Ebola vaccine development: Systemic review of pre-clinical and clinical studies, and meta-analysis of determinants of antibody response variability after vaccination." (2018) International Journal of Infectious Diseases 74:83-96.
Preston et al. "Lyophilized Filovirus Glycoprotein Vaccines: Peroxides in a vaccine formulation with polysorbate 80-containing adjuvant are associated with reduced neutralizing antibody titers in both mice and non-human primates." (2022) Journal of Pharmaceutical Sciences 111:3424-3434.
Preston et al. "Single-vial filovirus glycoprotein vaccines: Biophysical characteristics and immunogenicity after co-lyophilization with adjuvant." (2021) Vaccine 39:5650-5657.
Orr et al. "Elimination of the Cold-Chain Dependence of a Nanoemulsion Adjuvanted Vaccine Against Tuberculosis by Lyophilization." (2014) Journal of Controlled Release 177: 20-26.
Kramer et al. "Development of a Thermostable Nanoemulsion Adjuvanted Vaccine Against Tuberculosis Using a Design-of-Experiments Approach." (2018) International Journal of Nanomedicine 13: 3689-3711.
Chan et al. "Lyophilization of Adjuvanted Vaccines: Methods for Formulation of a Thermostable Freeze-Dried Product." Methods in Molecular Biology vol. 1494. Christopher B Fox (ed.). (2017) Vaccine Adjuvants: Methods and Protocols. Chapter 15; p. 215-226.

* cited by examiner

Effect of immunogen and adjuvant doses on antibody titers to EBOV GP in mice

FIG. 10

12 Week Incubation

COMPOSITIONS AND METHODS OF MANUFACTURING TRIVALENT FILOVIRUS VACCINES

RELATED APPLICATIONS

This application is a continuation application which claims priority from U.S. patent application Ser. No. 16/879,668 filed on May 20, 2022, now U.S. Pat. No. 11,433,129, which claims the benefit of priority from U.S. Provisional Application No. 62/850,443 filed on May 20, 2019, the contents of which are hereby incorporated by reference herein.

FIELD OF THE INVENTION

The invention relates to the field of recombinant vaccine compositions combined with a lyophilized nano-emulsion adjuvant. The invention also relates to methods of making and using the recombinant, mono- or multivalent vaccine compositions described herein. The invention specifically describes the novel combination of antigen and nano-emulsion adjuvant subjected to co-lyophilization to produce a thermostabilized, adjuvanted vaccine which is reconstituted with a pharmaceutically acceptable diluent immediately prior to use. Specifically, this invention relates to a recombinant non-replicating vaccine for filoviruses as well as similar formulations containing at least one viral glycoprotein antigen co-lyophilized with a nano-emulsion adjuvant.

BACKGROUND OF THE INVENTION

While the frequency of human infection remains relatively minimal compared to other viruses, the extreme virulence and mortality risk of filoviruses makes such infections an important target for vaccine development. Despite significant progress with the clinical development of several specific vaccine candidates and therapeutics during and after the West African outbreak (2013-2016), only one vaccine targeting Zaire ebolavirus (EBOV), but no vaccines targeting Sudan ebolavirus (SUDV), the Marburg marburgvirus (MARV) or other filoviruses have received regulatory approval. Moreover, protection of a monovalent EBOV vaccine against other filoviruses has never been demonstrated in relevant primate challenge studies requiring the development of additional monovalent or multivalent filovirus vaccines.

Filoviruses are enveloped, negative strand RNA viruses. The viral RNA is packaged with viral nucleoprotein (NP) and the envelope is formed by the association of the viral matrix proteins VP40 and VP24 with the membrane containing the mature surface glycoprotein (GP). GP has been identified as the viral protein leading to cell surface binding and membrane fusion and has therefore been selected as the major candidate antigen which may also induce virus neutralizing antibodies.

Vaccines containing recombinant proteins require an adjuvant to elicit a durable immune response (Callahan, Shorter, et al., 1991, The importance of surface charge in the optimization of antigen-adjuvant interactions, Pharm Res, v8:851-8). Adjuvants are molecules, compounds, or macromolecular complexes that boost the potency and longevity of specific immune response to antigens, but cause minimal toxicity or long-lasting immune effects on their own. Adjuvants can be used to enhance immunogenicity, modulate the type of immune response, reduce the amount of antigen or the number of immunizations required, and improve the efficacy of vaccines in newborns or elderly. To be maximally effective, adjuvants must be selected judiciously and formulated appropriately based on the desired immune response. However, the number of adjuvants with acceptable efficacy and safety profiles is limited.

The present state of the art in developing subunit protein immunogens for human vaccines is to utilize aluminum adjuvants as the starting point. The use of aluminum adjuvants is thus fostered by the fact that the record of safety of newer formulations cannot match the long term acceptability of aluminum adjuvants in human vaccines. Overall, this has amounted to a lack of advanced adjuvants that can be applied to vaccine development, coupled with the fact that several of the most advanced adjuvant formulations/compounds are the property of large pharmaceutical companies. Aluminum-salt adjuvants are currently the most widely used adjuvants for general use in humans. Aluminum adjuvants are considered relatively weak, effective in generation of neutralizing antibodies against certain bacterial antigens, but relatively ineffective at inducing long-lasting cellular immune responses.

The emerging trend in subunit vaccine development has been that it is insufficient to engineer the protein target itself, but that potent, safe, adjuvant formulations must be utilized as an intrinsic component of vaccine design, from the earliest feasibility experiments through clinical testing. The use of formulation technology can result in a significant decrease in dose levels and number of vaccinations, an increase in the quality and breadth of the immune response, as well as long-term, sustained responses to the antigenic target.

Multivalent vaccine compositions are known in the art and have been described in the literature.

WO1993/024148 discloses an invention of multivalent vaccine containing antigens IPV-DPT-Hib-Hepatitis B wherein DPT is adsorbed to AlOH or aluminum phosphate and Hib is adsorbed to only aluminum phosphate, wherein the Hib antigen is used extemporaneously by mixing to the other antigens just prior to the administration.

WO1997/00697 discloses a DPT-Hib and pertussis multivalent vaccine adsorbed to aluminum phosphate, in which one container has a freeze-dried vaccine and the other container comprises a second antigen.

WO1998/000167 discloses a DTaP-IPV-Hib antigen vaccine and WO1999/13906 describes a multiple component vaccine in which certain components may be reconstituted from a lyophilized state by the other components of the vaccine, or may exist in a single solution, and administers the vaccine in a specially designed container at the time when the vaccination is performed.

WO2000/07623 describes a multi-component vaccine composition having acellular pertussis vaccine components (PT and FHA), diphtheria toxoid (DT), tetanus toxoid (TT), a conjugate of a capsular polysaccharide of *Haemophilus influenzae* type b and tetanus toxoid or diphtheria toxoid (Hib), Hepatitis B Surface Ag (HBsAg) and inactivated poliovirus (IPV) which may be in a single solution, or certain components may be reconstituted from a lyophilized state by the other components of the vaccine.

WO2002/000249 discloses a capsular polysaccharide of *Haemophilus* influenza type b not adsorbed onto an aluminum adjuvant salt, and two or more further bacterial polysaccharides which may include whole cell pertussis, tetanus toxoid, diphtheria toxoid, Hepatitis B surface antigen (HbsAg), and/or conjugate polysaccharides of *N. meningitides* type A, or B, or C as antigens in a single quadrivalent and/or trivalent vaccine.

WO2006/097851 discloses a multivalent vaccine which can be prepared extemporaneously at the time of use by mixing together two components the first component comprising D, T, wP and HBsAg antigens and a second component comprising a Hib conjugate and one or more meningococcal conjugates.

WO2007/054820 relates to a vaccine composition wherein the D, T, and aP antigens are specifically adsorbed on aluminum hydroxide and the Hib and the Hep B antigens are adsorbed onto aluminum phosphate which do not exist in a fully liquid stable composition.

WO2008/044611 discloses a method for the preparation of a mixed IPV-DPT vaccine comprising an inactivated poliovirus Sabin strains type I, II, and III grown in Vero cells, a protective antigen against *Bordetella pertussis*, a diphtheria toxoid and a tetanus toxoid, which involves the step of producing a poliovirus Sabin strain having a high titer.

WO2019/051098 discloses the production and evaluation of a recombinant subunit filovirus vaccine using insect cell expressed surface glycoprotein (GP) and a highly effective adjuvant. The vaccine provides protection in humans against filovirus infection, including Ebola virus and Marburg virus, but requiring CoVaccine-HT™ as the adjuvant of choice.

Most other vaccine platforms used for filoviruses are either based on recombinant virus vectors with a GP antigen, pseudo-typed replication incompetent viruses or virus-like particles. The vaccine candidate of the present invention is the only approach based on native, immunoaffinity-purified recombinant protein subunits. There remains a need in the art for a novel, safe and effective vaccine that can be produced in a quantity sufficient to protect first responders, healthcare and laboratory workers, the military, and the civilian population, while simultaneously being capable of acquisition into strategic stockpiles. Furthermore, as the causative agent in a future public health emergency is not known, a multivalent vaccine will better meet the needs than single-agent products.

Thermostabilization of proteins with lyophilization is well understood. Moreover, technologies to thermostabilize alum-adjuvanted protein subunit vaccines without inducing undue agglomeration or aggregation have also been demonstrated (WO2008/118691 and WO2012/158978). However, alum is less effective at stimulating cell-mediated immune responses and is not therefore sufficient for all vaccines. The nano-emulsion adjuvant CoVaccine-HT™ has been previously tested as a prepared liquid emulsion (Blom et al., Sucrose fatty acid sulphate esters as novel vaccine adjuvants. Effect of chemical composition. *Vaccine* 2004; 23:743-54; Hilgers et al., Sucrose fatty acid sulphate esters as novel vaccine adjuvant. *Vaccine* 24S2 (2006) S2/81-S2/82). Lyophilization of nano-emulsions has been conducted previously, however lyophilization of a vaccine nano-emulsion adjuvant, maintaining immunogenicity after lyophilization, has not been demonstrated. Similarly, co-lyophilization of a nano-emulsion mixture with one or more separate proteins has also not been demonstrated.

SUMMARY OF THE INVENTION

The present invention provides for a stable immunogenic composition capable of eliciting a robust and durable immune response, comprising at least one antigen further comprising a viral glycoprotein and at least one nano-emulsion adjuvant which are co-lyophilized and can be reconstituted immediately prior to use. In an alternative embodiment, the present invention provides for a vaccine composition comprising at least two antigens, wherein each antigen is specific to a different genus of filovirus and which also comprises at least one nano-emulsion adjuvant. Preferably, the viral glycoprotein is at least one selected from the group of viruses consisting of MARV, SUDV and EBOV. Optionally, the viral glycoprotein is a filovirus glycoprotein.

In another aspect, the present invention provides for a stable, immunogenic composition capable of eliciting a robust and durable immune response, comprising at least one antigen, wherein the at least one antigen comprises a viral glycoprotein, and at least one adjuvant. Optionally, the composition does not include alum.

Alternatively, the composition of the present invention comprises two or more antigens, wherein each antigen is specific to a different virus.

In yet another aspect, the composition of the present invention further comprises a nano-emulsion adjuvant, wherein the nano-emulsion, preferably, is CoVaccine-HT™. In a preferred embodiment, the nano-emulsion adjuvant is mixed with the antigen prior to lyophilization. Preferably, the nano-emulsion adjuvant that is mixed is CoVaccine-H™.

Another aspect of the invention provides for a method of manufacturing a stable immunogenic composition capable of eliciting a robust and durable immune response to more than one virus, comprising at least two antigens, wherein each antigen is specific to a different virus from the same or different families and providing at least one adjuvant, wherein the adjuvant does not contain alum. Preferably, the adjuvant is a nano-emulsion and, most preferably, the adjuvant is CoVaccine-HT'. Alternatively, the adjuvant is combined with the antigen(s) prior to lyophilization. Preferably, the adjuvant to be combined is CoVaccine-HT'.

In another aspect, the present invention provides for a method of eliciting an immune response in a mammal comprising: (a) providing a stable, immunogenic composition capable of eliciting a robust and durable immune response, comprising at least one antigen, wherein the at least one antigen comprises a viral glycoprotein, and at least one adjuvant; (b) reconstituting the composition of (a) prior to use with a pharmaceutically acceptable diluent; and (c) administering the composition to the mammal in need thereof. Preferably, the composition is administered up to three separate occasions, resulting in the mammal being protected from subsequent infections by the virus associated with the viral glycoprotein present in the composition.

In yet another aspect of the present invention provides for a stable immunogenic composition capable of eliciting a robust and durable immune response, comprising at least one nano-emulsion adjuvant, wherein the at least one nano-emulsion adjuvant is lyophilized and can be reconstituted immediately prior to use with an antigen.

BRIEF DESCRIPTION OF THE DRAWINGS

The following figures provide illustrative examples of the present invention and are incorporated by reference within this disclosure.

Figures 2, 3:
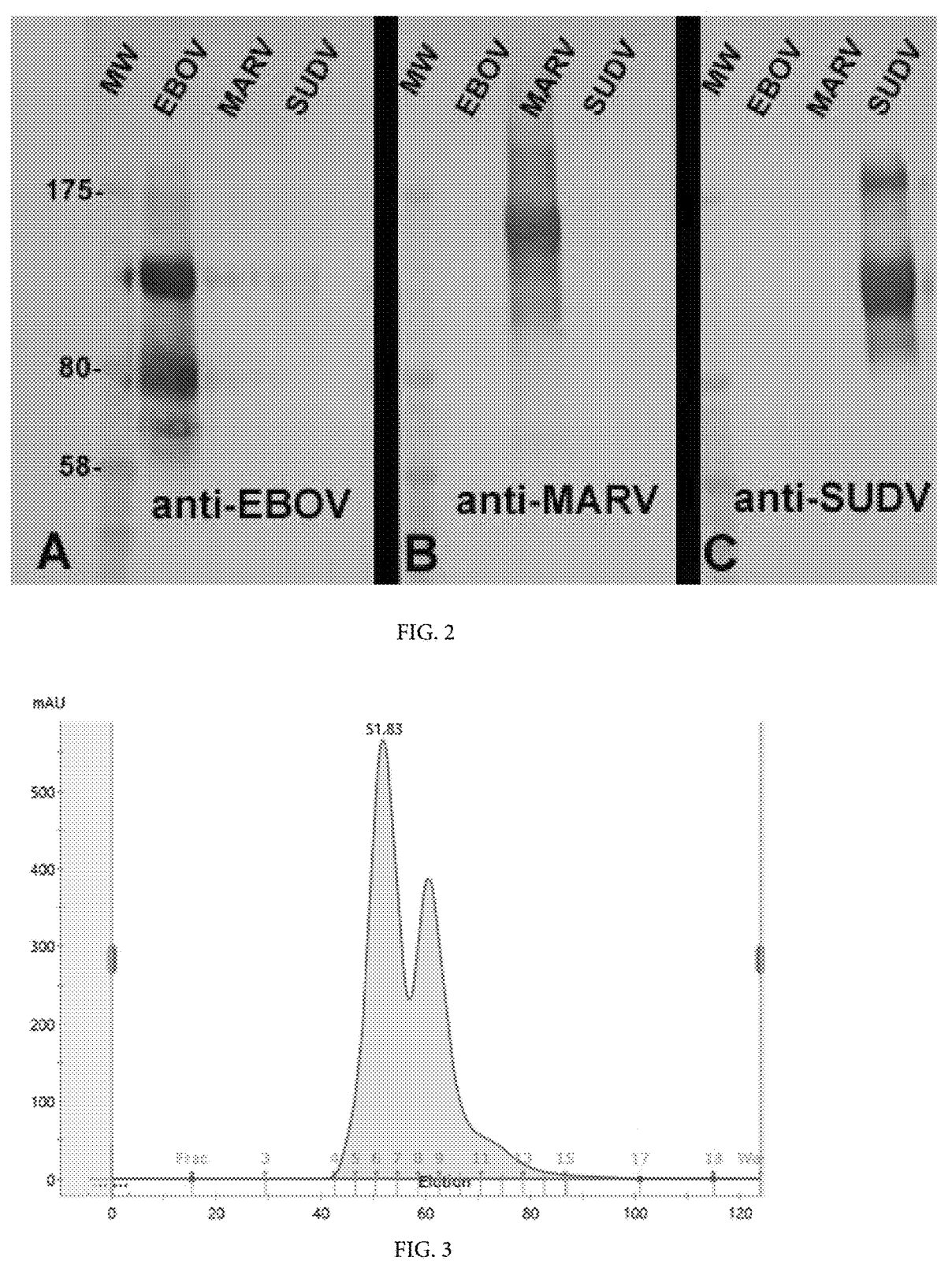

FIG. 2 shows identical Western-blot panels of purified E-GP, M-GP and S-GP, which were generated and probed by EBOV, MARV and SUDV-specific monoclonals demonstrating viral specificity.

FIG. 3 shows a chromatogram showing size-exclusion-chromatography of IAC-purified E-GP. The blue graph shows A280 extinction; retention times of the two peaks represent trimers (right peak) and dimers of trimers (left peak), respectively.

Figures 8A, 8B:
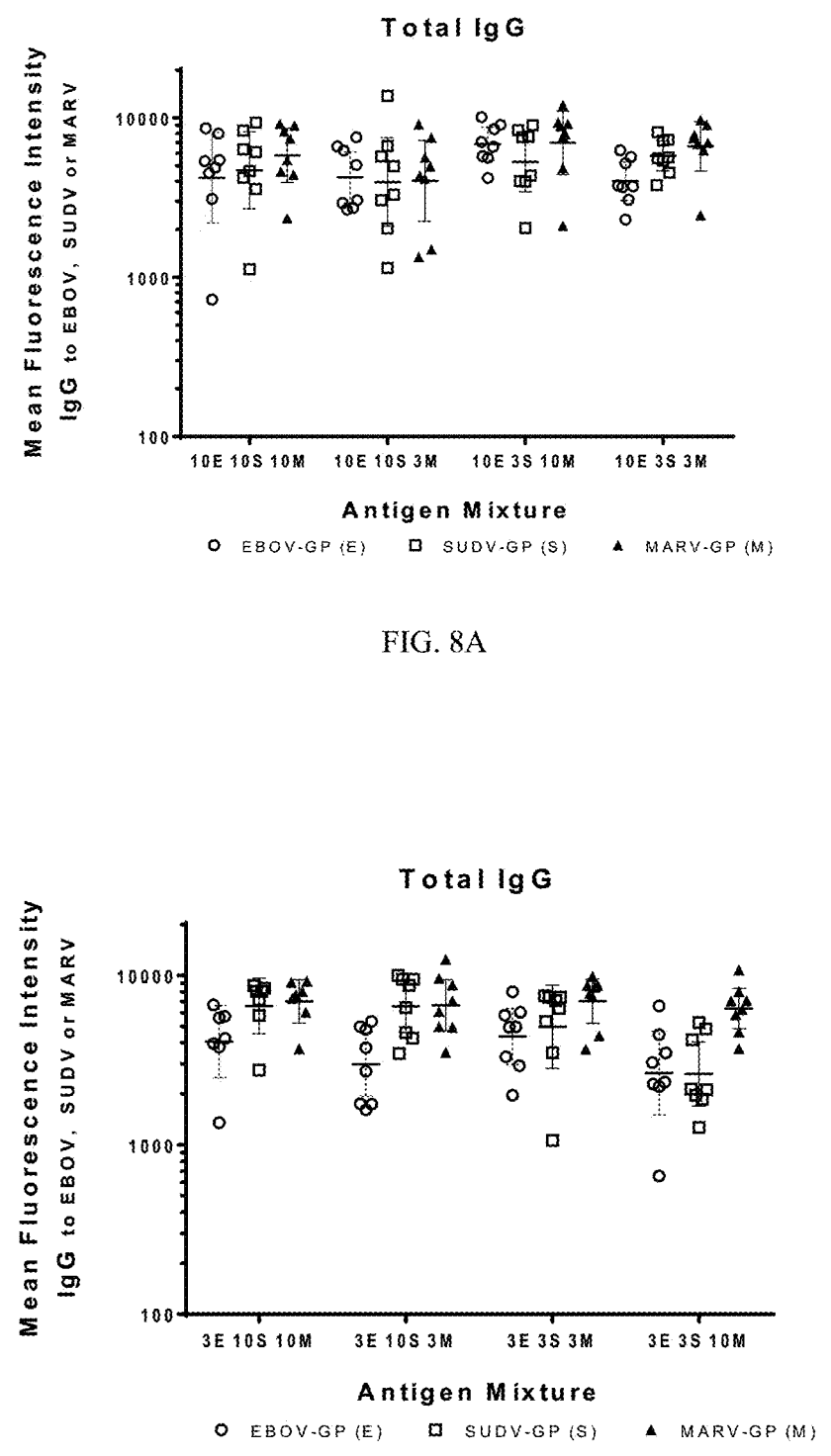

FIGS. 8A and 8B depict results of Mouse Antigen balancing experiment; 8A: Mouse groups immunized with 10 µg of E-GP and either 3 or 10 µg of S-GP and M-GP; 8B: Mouse groups immunized with 3 µg of E-GP and either 3 or 10 µg of S-GP and M-GP.

FIG. 10 depicts the immunogenicity of CoVaccine-HT™ at 3, 5, 7 and 10 mg/ml co-lyophilized with EBOV GP protein (0.01 or 0.1 mg/ml) and 9.5% w/v trehalose and 10 mM ammonium acetate adjusted to pH 7. Immunogenicity is the same whether generated with the co-lyophilized product or the individual proteins augmented with the liquid nano-emulsion CoVaccine-HT™ product.

FIG. 11 depicts antibody titers in male and female Swiss Webster mice after vaccination with liquid and lyophilized MARV-GP formulations mixed with CoVaccine-HT™ after reconstitution and prior to administration on Days 0, 21 and 42 and blood collection on Day 56.

Figure 12A:
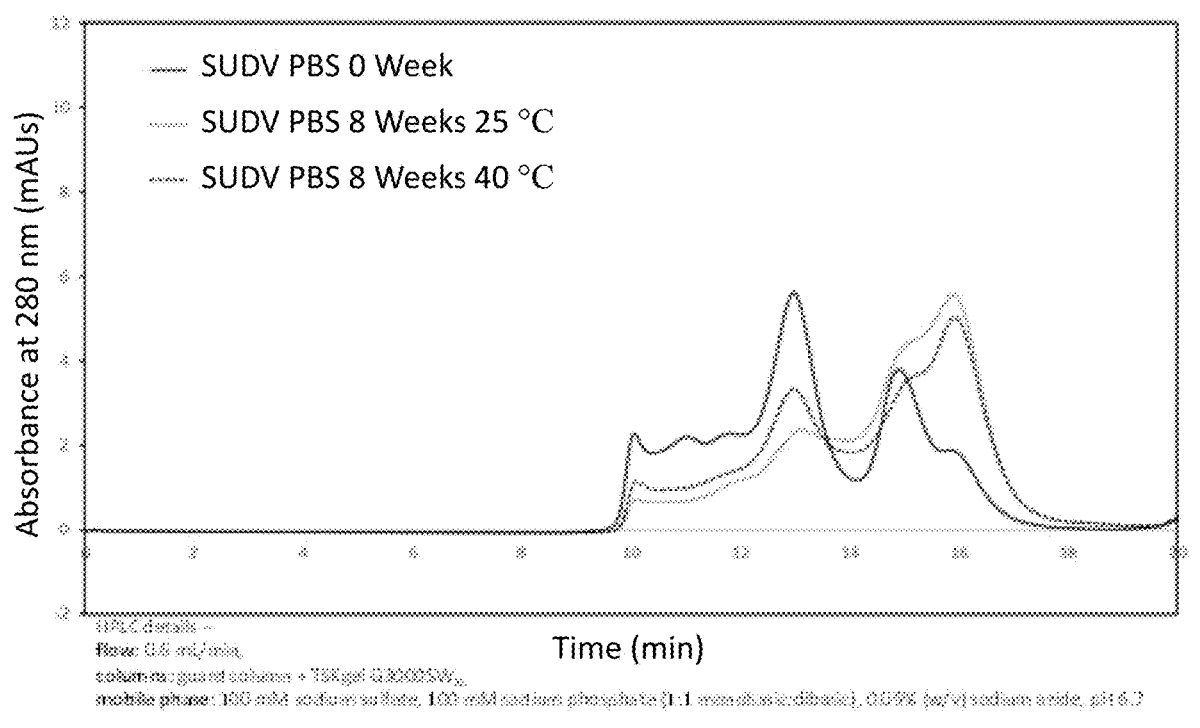
Figure 12B:
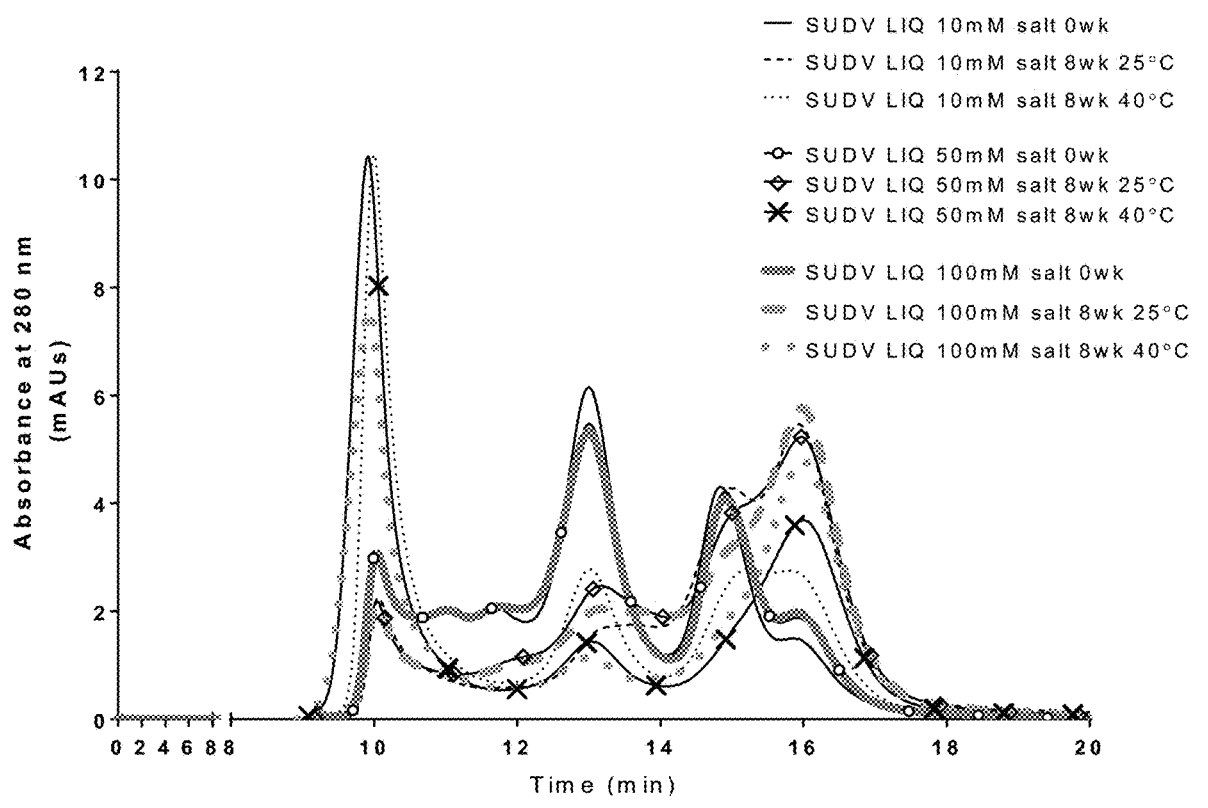
Figure 12C:
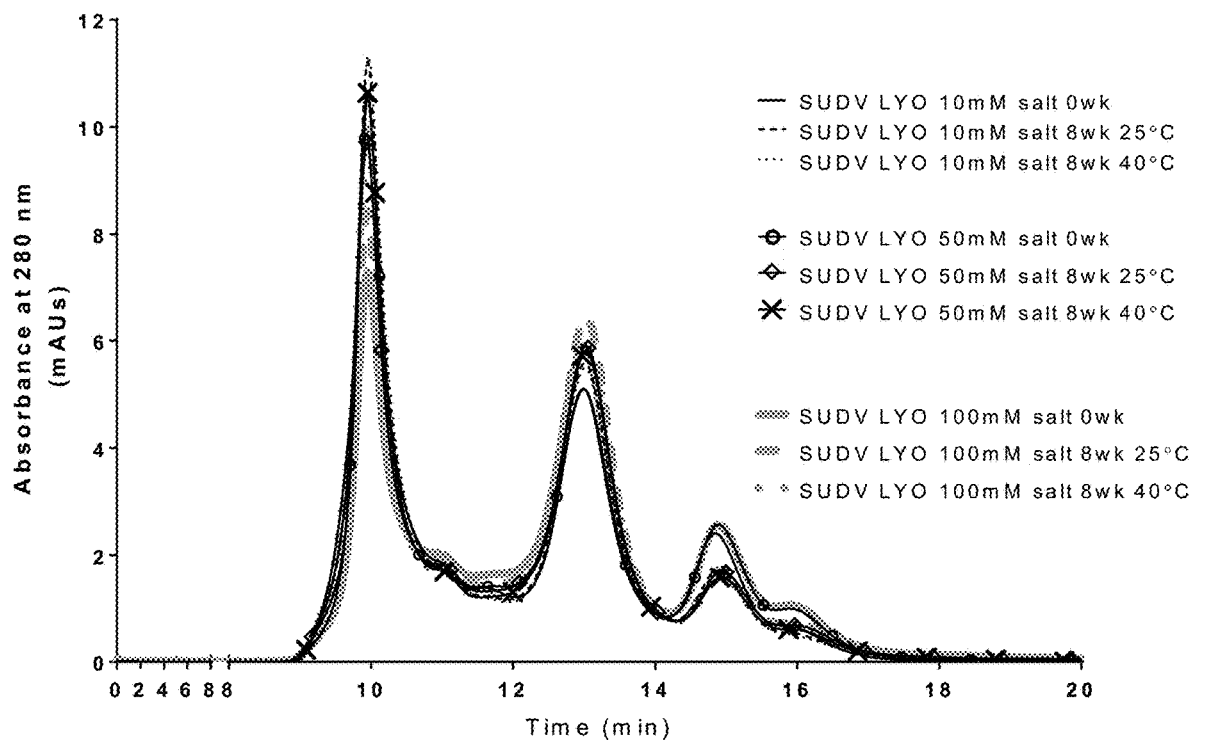

FIGS. 12A, 12B and 12C depict the stability of SUDV-GP preparations when stored in PBS, in the liquid formulation (without lyophilization) and in the liquid formulation (after lyophilization). Size exclusion chromatography of the samples immediately after formulation as well as after 8 weeks storage at 40° C. are demonstrated. The higher molecular weight entities, represented by peaks at earlier time points, are believed to be more important for protective immunogenicity. The lyophilized samples maintained the aggregation profile (16C) whereas the PBS (16A) and liquid formulation (16B) samples showed evidence of degradation with decrease in high molecular weight entities and increase in monomeric protein entities.

FIGS. 13A, 13B, 13C and 13D depict the immunogenicity of various mixtures of viral glycoproteins lyophilized with and without the CoVaccine-HT™ adjuvant. For mixtures lyophilized without adjuvant, adjuvant was added upon reconstitution and before administration to the mice. Data show the immunogenicity (Immunoglobulin G concentration in serum) recognizing EBOV GP, MARV GP and SUDV GP respectively generated in blood collected 2 weeks after the $3^{rd}$ dose of vaccine. Groups in the x-axis are identified by formulation conditions with E=EBOV GP, M=MARV GP and S=SUDV GP. FIG. 13A shows the results of Groups 1-12 from Table 6, FIG. 13B shows the results of Groups 13-24 from Table 6, FIG. 13C shows the results of Group 25-30 from Table 6 and FIG. 13D shows the results of Groups 31-36 from Table 6.

FIGS. 14A, 14B and 14C depict the differences in protein characteristics across the EBOV GP, MARV GP and SUDV GP proteins respective. In FIG. 14A, representative size-exclusion chromatogram of unincubated EBOV-GP liquid in PBS formulation (black) and 4-week incubated liquid in PBS at 40° C. (blue). Peak classifications were made using SEC-MALS molecular weight data (gray markers, right axis). High molecular weight (HMW) species were defined peaks that eluted between 9 and 12.3 minutes, monomer was defined as peaks eluting between 12.3 and 13.9 minutes, and monomer folding variants were defined as the peaks eluting between 13.9 and 17.3 minutes. The molecular weights of the species eluting in each of the peaks were identified using SEC-MALS, with molecular weights shown as gray markers on the right axis. In FIGS. 14B and 14C, representative chromatograms are shown for MARV-GP and SUDV-GP with peak molecular weights from SEC-MALS analysis overlaid and shown as gray markers.

DETAILED DESCRIPTION OF THE INVENTION

Figure 1:
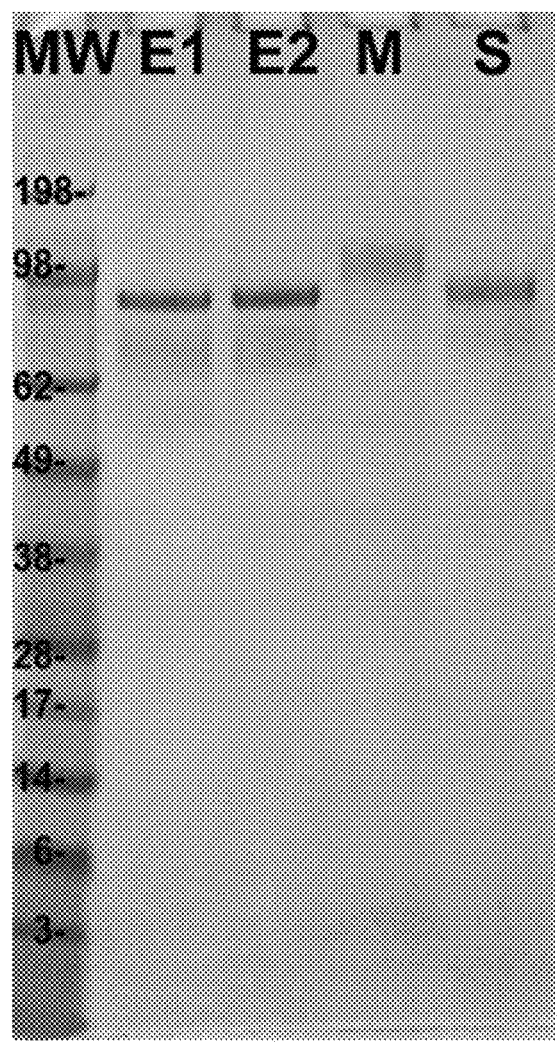
FIG. 1 depicts a Coomassie stained SDS-PAGE gel (4-12%) showing Molecular weight standard MW (sizes in kDa), followed by 1 μg each of single step IAC purified EBOV GP (two batches, E1 & E2), MARV GP (M) and SUDV GP (S).

Despite significant progress with the clinical development of several EBOV vaccine candidates and therapeutics during and after the West African outbreak, only one vaccine targeting EBOV and none targeting other filoviruses have received regulatory approval. Moreover, protection of a monovalent EBOV vaccine against other filoviruses has never been demonstrated in relevant primate challenge studies requiring the development of additional monovalent or multivalent filovirus vaccines.

We present data of a trivalent vaccine based on recombinant filovirus glycoproteins (GP) from EBOV, MARV and SUDV produced using the *Drosophila* S2 platform. The highly purified recombinant subunits elicit potent immune responses in mice, guinea pigs and non-human primates (NHPs) and consistently produce high antigen-specific IgG and surrogate virus neutralizing antibody titers.

Candidate vaccines show full protection against EBOV infection in rodent and NHP challenge models. Similarly formulated monovalent MARV or SUDV vaccine candidates can protect cynomolgus macaques completely against infection with lethal doses of MARV or SUDV and combinations with the EBOV vaccine can be formulated yielding multivalent vaccines retaining efficacy.

Ongoing formulation focuses on thermostabilization of recombinant subunits by lyophilization. Current data suggest that shelf stability of at least three months at 40° C. is feasible for each of the three antigens individually. Most importantly, formulations of antigens lyophilized in the presence of adjuvant are also stable, which should enable clinical development of safe and efficacious, field-deployable vaccine candidates for protection against Ebola, Marburg and Sudan Virus Disease. While thermostabilization of subunit proteins upon lyophilization with alum adjuvants has been demonstrated, the use of nano-emulsion vaccines in this context has not been previously successfully demonstrated. We have demonstrated that the nano-emulsion adjuvant can not only be lyophilized alone and then reconstituted and still retain immunogenicity, but that it can be lyophilized with a subunit protein under specific formulation conditions and maintain immunogenicity.

The present invention describes a solid multivalent filovirus protection in NHPs, which can be achieved with an adjuvanted formulation featuring a balanced combination of highly purified and defined recombinant filovirus protein antigens. Additional embodiments include improved conditions to allow the final product to be stored under the most economical conditions without risking loss of immunogenicity or efficacy. Furthermore, the core platform described herein will be applied to develop more complex multivalent vaccines that include antigens from emerging and re-emerging viruses, including but not limited to, Alphaviruses, Henipaviruses, Arenaviruses, pandemic and seasonal flu and coronaviruses.

In one aspect, the platform of the present invention is based on recombinant subunit filovirus proteins expressed by stably transformed *Drosophila* S2 cell lines for development of the trivalent filovirus vaccine candidate. Proper conformation of complex viral proteins is often problematic to achieve and the production system described herein has shown the ability to overcome the challenges and produce correctly folded viral glycoproteins with native conformation for a number of viral vaccine targets. An important advantage to this system is the capacity of the system to quickly and cost effectively generate production scale quantities of high quality viral proteins from stably transformed cell lines that are key to producing humoral and cellular immune responses and protective efficacy. This recombinant approach is unique among the filovirus vaccines currently in development, particularly as we use highly purified subunit proteins with a safe, advanced clinical adjuvant and have demonstrated potent efficacy against EBOV infection in the gold standard cynomolgus macaque model. The novel approach described herein is based on highly purified recombinant subunits that provide the unique opportunity to fine-tune the immune response by varying the composition and dosage of individual viral antigens to achieve the desired broad-spectrum immunity. Similarly balanced immunity is very difficult, if not impossible, to achieve for virally vectored platforms, DNA vaccines, and even VLP's.

In another embodiment, the recombinant subunit vaccine platform of the present invention achieves the high quality of its antigens by the use of antigen-specific immunoaffinity chromatography (IAC) which rejects any protein with misfolded epitope regions. Therefore, there is a need for sufficient quantities of antibodies produced under conditions that lend themselves to rapid, cost-effective GMP manufacturing.

EXAMPLES

The following examples illustrate the various embodiments of the present invention and are not meant to be limiting in scope based on such examples.

Expression and Purification of Subunit Proteins:

All antigens used for the studies described herein have been expressed using stably transformed *Drosophila* cell lines in 1-5L batches in a WAVE bioreactor (GE Lifesciences, Piscataway, N.J.). Expression levels of all selected cell lines (for MARV-GP after two rounds of subcloning) have been stable in the range of 10-100 mg/L. The GP subunits were subsequently purified by single-step immunoaffinity chromatography (IAC) using specific affinity columns for each individual protein (see FIG. 1). To date, more than 200 mg of EBOV GP (E-GP), 100 mg of MARV GP, and 100 mg of SUDV GP with purity levels between 90-95% (based on SDS-PAGE) have been produced. EBOV, SUDV and MARV GP's are highly pure and show good antigenic specificity (FIG. 2).

To establish the equivalency of plant- and murine hybridoma-derived monoclonal antibodies, we tested a plant- and hybridoma-derived anti-GP antibody (13C6—description can be found in Olinger et al. 2012). A 1.5ml column containing 15 mg of immobilized plant-expressed antibody bound 0.2 mg antigen per batch while a column using hybridoma-derived antibody (100 mg immobilized on 10 ml NHS-sepharose) bound between 1-1.3 mg per batch proving that the plant-expressed antibody achieves similar yields and purity (>90%) of E-GP. We now routinely use plant-expressed monoclonal antibodies for production of filovirus GPs. When analyzing the size of purified E-GP, we discovered that it mainly forms trimers (native conformation on virus particles) as well as dimers of trimers (FIG. 3). We separated the two populations of oligomers by FPLC and established their protective potential in guinea pigs as identical (Lehrer et al., Recombinant Subunit Vaccines Protect Guinea Pigs From Lethal Ebola Virus Challenge. *Vaccine* 2019; November 8; 37(47):6942-6950). We therefore don't think that a polishing step will be required in establishing our final antigen purification procedure.

Immunogenicity and Efficacy in Mice:

Immunogenicity of purified EBOV GP subunits was tested in Balb/c mice. First, individual antigens were tested in formulations with four functionally different adjuvants: ISA-51 (water-in-oil emulsion; Seppic, Fairfield, N.J.), GPI-0100 (saponin-based; Hawaii Biotech, Inc., Honolulu, Hi.), CoVaccine-HT™ (emulsion-based; BTG, London, UK) and Ribi R-700 (monophosphoryl lipid A and trehalose dicorynomycolate; Sigma-Aldrich). Excellent humoral and cell-mediated responses were seen, especially for CoVaccine HT™ and GPI-0100 (data not shown). ELISA antibody responses to the antigens were evident after one immunization, and as expected, increased following a booster injection. E-GP administered at doses from 1-9 µg showed a typical dose-related response (Lehrer et al., Recombinant proteins of Zaire ebolavirus induce potent humoral and cellular immune responses and protect against live virus infection in mice. *Vaccine* 2018; 36(22):3090-3100).

For the first efficacy study, Balb/c mice were immunized at days 0, 28 and 56 with formulations containing IAC purified recombinant E-GP with or without adjuvants. The animals were infected 23 days after the third immunization by i.p. injection with 100 pfu (3000 LD50) of mouse adapted EBOV (MA-EBOV). The results of the experiment are shown in Table 1.

TABLE 1

Recombinant Ebola virus GP subunits protect mice against live virus challenge

| Group no. | Immunogen[a] | Adjuvant | Survival (day 20 post challenge)[b] | Morbidity[c] |
|---|---|---|---|---|
| 1 | GP | NONE | 70% | All survivors sick |
| 2 | GP | GPI-0100 | 90% | All survivors sick |
| 3 | GP | CoVaccine HT | 100% | None sick |
| 4 | NONE | NONE | 0% | No survivors |

TABLE 1-continued

Recombinant Ebola virus GP subunits protect mice against live virus challenge

| Group no. | Immunogen[a] | Adjuvant | Survival (day 20 post challenge)[b] | Morbidity[c] |
|---|---|---|---|---|
| 5 | NONE | GPI-0100 | 10% | Survivor sick |
| 6 | NONE | CoVaccine HT | 0% | No survivors |

[a]Mice were immunized with 10 μg antigen (s.c.)
[b]10 animals per group, except groups 4 and 6 with 9 animals each.
[c]Morbid (sick) animals showed any signs of illness (e.g. ruffled fur).

Interestingly, animals immunized three times with 10 μg of EBOV GP (no adjuvant) showed 70% protection, similar to protection reported after four doses of the best adjuvanted formulations of recombinant "Ebola immune complexes" (Phoolcharoen et al. 2011) and also similar in protection achieved with four doses of a recombinant GP-Fc fusion protein administered to mice in Freund's adjuvant (Konduru et al. 2011), but significantly better than protective efficacy of Novavax's GP nanoparticles when given alone or in combination with Alum (Bengtsson et al. 2016). GP formulated with CoVaccine-HT' showed 100% protective efficacy against both morbidity and mortality emphasizing the importance of adjuvant selection for protection. The excellent protective efficacy of the adjuvanted formulations, in combination with the finding of surprisingly good protective efficacy with unadjuvanted GP, strongly support the use of this protein as a vaccine candidate. In comparison, with and without adjuvant, recombinant GP yields immune responses equivalent or superior to responses seen with Ebola virus-like particles (VLPs) in mice (Warfield et al. 2003, 2007), without the production challenges associated with VLPs that are being produced similarly to viruses using centrifugation methods and are prone to be affected by batch-to-batch consistency and stability issues.

Recombinant EBOV GP Subunit with CoVaccine Adjuvant Elicits Protective Cellular and Humoral Responses:

To evaluate the humoral and cellular immune mechanisms underlying protection conferred by GP, a further study employing passive protection by transfer of immune serum and adoptive protection by transfer of immune T-cells was conducted. A formulation containing 10 μg E-GP protein and CoVaccine-HT™ was administered three times at 4-week intervals to 35 Balb/c mice. Fourteen days after the last dose, 30 mice were euthanized and serum samples collected by cardiac puncture. Samples from all animals were pooled, and then 1 ml immune serum each was transferred i.p. to naïve Balb/c mice. Splenocytes were prepared from the spleens of vaccinated mice and T-cells separated by negative selection (using MACs separation (Invitrogen, Carlsbad, Calif.)). T-cells were transferred at two dose levels. All mice, including the remaining five vaccines ("direct challenge") were infected approximately 24 hours post serum/splenocyte transfer by i.p. injection with 1000 pfu (30000 $LD_{50}$) of MA-EBOV. Surviving animals were euthanized 28 days post challenge and serum samples collected. Pre-challenge sera collected from immunized mice during the immunization phase were analyzed for antigen specific ELISA IgG titers. GP immunized mice showed GMT $EC_{50s}$>100,000 after two and three doses. Survival is shown in Table 2.

TABLE 2

Passive transfer of serum or adoptive transfer of immune T cells protects naïve Balb/c mice against challenge with MA-EBOV (# survivors/total # challenged)

| Vaccine | Direct Challenge | Serum Transfer[1] | T cells (high[2]) | T cells (low[3]) |
|---|---|---|---|---|
| 10 μg GP + CoVaccine HT | 5/5 >102400 (GP[4]) | 9/10 | 7/10 | 5/10 11324 (GP) |
| CoVaccine HT | 0/5 | 0/10 | — | — |

Figure 4:
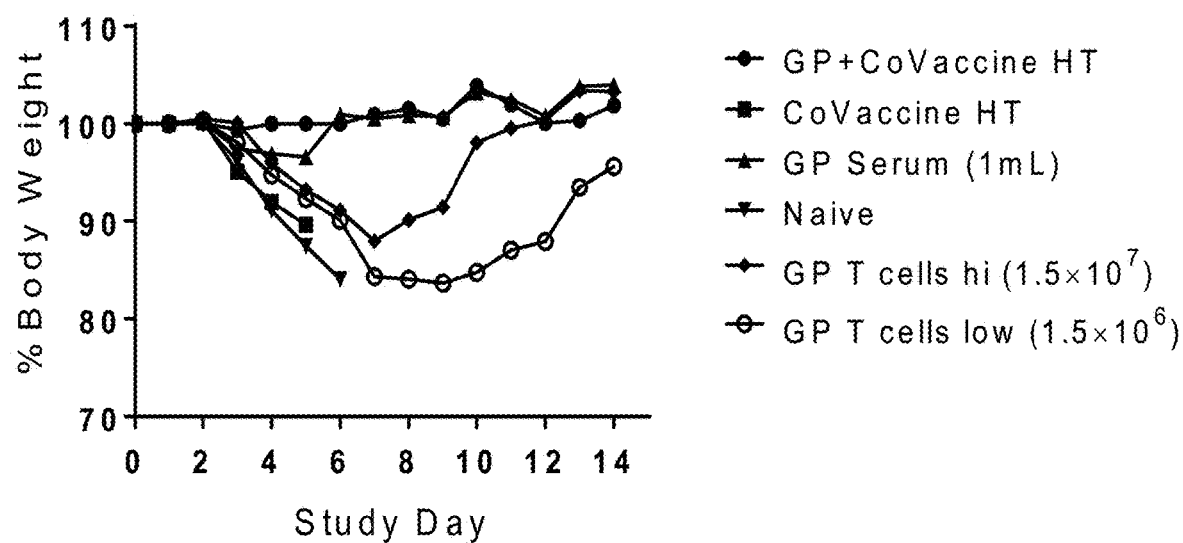
FIG. 4 depicts active or passive immunization protects mice against weight loss post challenge with ma-EBOV. Body weights normalized to animal's weight at day 0 (challenge day) are plotted. Directly challenged vaccines as well as animals receiving anti-GP serum show the least morbidity; survivors in T-cell transfer groups showed some malaise but full recovery by day 14 post challenge.

[1]1 ml of immune serum per mouse administered i.p.
[2]1.5 × 10⁷ T-cells/mouse administered i.p.
[3]1.5 × 10⁶ T-cells/mouse administered i.p.
[4]anti-GP IgG titer (GMT EC50) 28 d post challenge Direct challenge controls showed full protection as previously seen. As expected, GP-specific antiserum provided almost complete protection to the naïve recipients. Interestingly, the protected animals receiving GP-specific serum as well as the directly challenged GP-vaccines showed no weight loss (FIG. 4), which is seen as an indicator of morbidity in the mouse model (Bray et al. 1998). Furthermore, post-challenge ELISA titers on directly infected mice showed that anti-GP levels were in the same range as pre-challenge sera, while anti-VP40 titers stayed extremely low (~1.5 logs below VP40 titers observed in other post-challenge samples; data not shown). This suggests that very little, if any, viral replication occurred. We postulate further, that in passively immunized mice (serum transfer) the virus was effectively neutralized, eliminating morbidity. Immune T-cells were able to protect the majority of naïve recipients from death and a dose-dependency of survival and weight loss caused by infection could be seen. Post-challenge induction of GP and VP40-specific IgG responses in these naïve animals can be explained by a limited degree of viral replication. In sum, this experiment demonstrated that recombinant EBOV GP not only induces potent humoral responses, but also generates the critical functional cellular immune responses indicated by the ability of immune T cells to transfer protection to naïve mice (Lehrer et al., Recombinant proteins of Zaire ebolavirus induce potent humoral and cellular immune responses and protect against live virus infection in mice. *Vaccine* 2018; 36(22):3090-3100).

Non-Human Primate Immunogenicity and Efficacy:

Cynomolgus macaques (*Macaca fascicularis*) were chosen to conduct a non-human primate immunogenicity and efficacy experiment based on an EBOV challenge model originally developed by Dr. Thomas Geisbert at USMARIID (now Galveston National Laboratory/UTMB).

Figure 5:
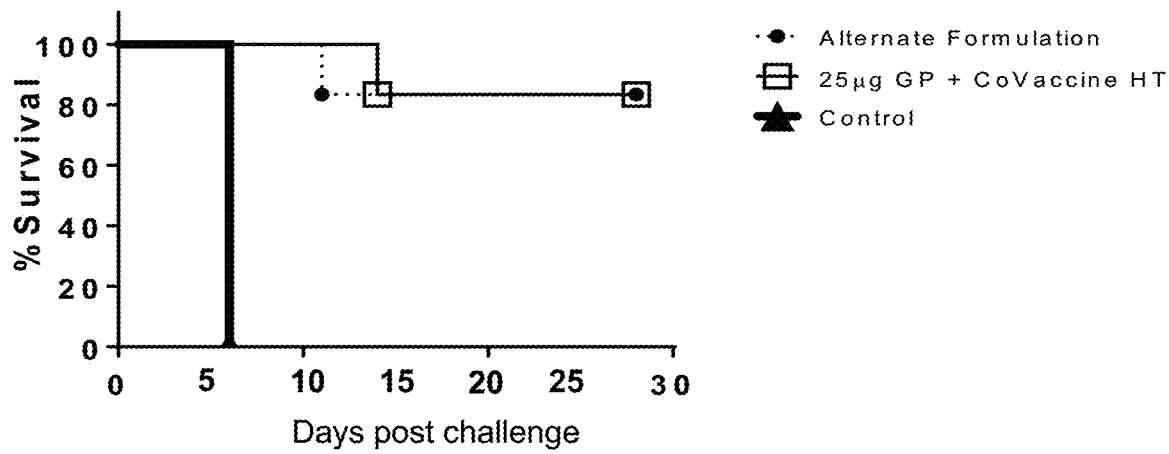
FIG. 5 shows survival of vaccinated and control monkeys (cynomolgus macaques) after live viral challenge with EBOV. Using either the Log-rank (Mantel-Cox) test or the Gehan-Breslow-Wilcoxon test, both of the curves for the vaccinated animals are significantly different from the controls (p=0.0082).

This experiment used animals of both sexes and older (5-15 years old) than typically used for EBOV challenge studies found in the literature (typically 3-4 years old). We believe that this better reflects a representative age distribution than basing development only on young adults. One group of animals was immunized by the intramuscular route (IM) three times at three week intervals with 25 μg of EBOV GP formulated with 10 mg of CoVaccine-HT™ adjuvant, a second group was immunized with an alternate formulation (containing GP with recombinant EBOV VP24 and VP40 proteins produced similarly to EBOV GP and using the same adjuvant), while the control group was given only adjuvant. Four weeks after the last vaccination, all animals were challenged by the subcutaneous route (SC) with 1000 $LD_{50}$ of EBOV, strain Kikwit (7U isolate 199510621, stock number R4414 (Kugelman et al. 2016). Animals were monitored twice daily for morbidity and mortality for up to 28 days. Results are given in Table 3 below and survival curves are shown in FIG. 5.

TABLE 3

Results from EBOV challenge study in cynomolgus macaques

| Group | Vaccine composition | # survivors/total # of animals challenged |
|---|---|---|
| 1 | 25 µg EBOV GP + 10 mg CoVaccine HT adjuvant | 5/6[a] |
| 2 | Alternate vaccine formulation[b] | 5/6 |
| 3 | Adjuvant only | 0/2 |

[a]The single animal that met the euthanasia criteria in group 1 was a 15-year-old male and did not show any signs of Ebola Virus Disease (EVD) (based on clinical chemistry and the necropsy report). The animal that had to be euthanized in group 2 was also a 15-year-old male who showed some clinical markers of EVD based on pathology observed in the necropsy.
[b]The alternate formulation contained EBOV GP + VP24 and VP40 proteins (produced and purified similarly to GP) with the same adjuvant.

Figure 6:
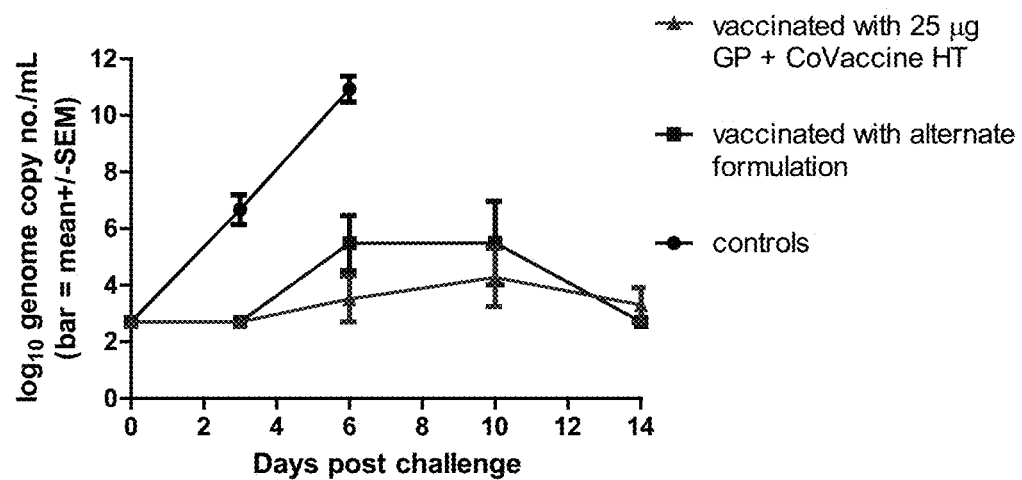
FIG. 6 depicts kinetics of viremia post challenge. Viremia was determined by rt-PCR on serum samples taken from individual animals post challenge—Limit of detection: 3 log 10.

Viremia was determined by rt-PCR. Sera from all animals were collected at 3-4 day intervals until death (controls) or day 14 (vaccines). The results are shown in FIG. 6, which clearly demonstrate the dramatic inhibition of viremia as a result of vaccination with the recombinant subunit monovalent Ebola vaccine. The animals vaccinated with the alternate formulation showed slightly higher virus load than animals vaccinated with GP+CoVaccine-HT™.

Figure 7:
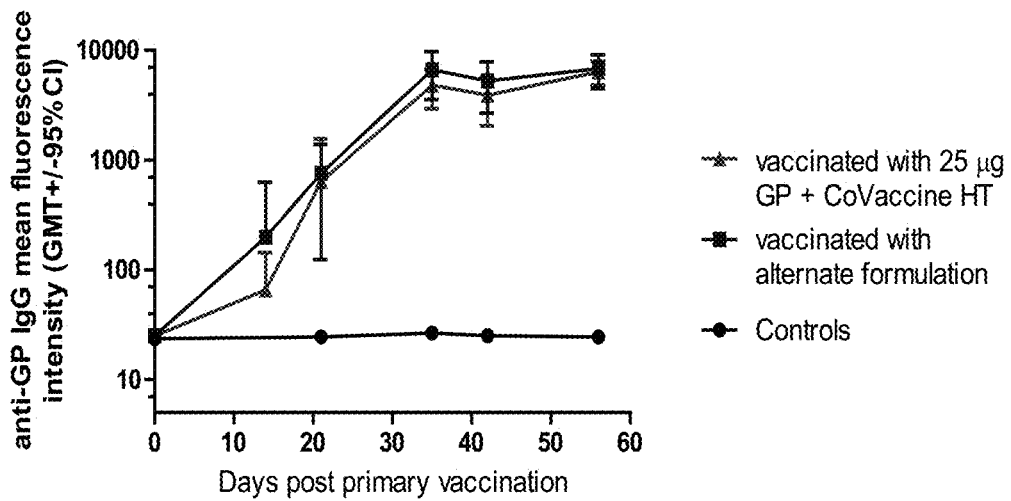
FIG. 7 shows IgG antibody titers to Ebola GP antigen determined by the MIA assay on vaccinated animals. Animals were immunized on days 0, 21, and 42. Antibody levels in vaccinated animals rose rapidly after the first and second immunizations and reached a plateau by 14 days post dose 2 (day 35).

Antibody titers were determined on serum samples from vaccinated animals at various time points post vaccination but prior to challenge. The results shown in FIG. 7 demonstrate a robust humoral immune response. There is no statistically significant difference between titers elicited by either vaccine formulation.

The results of the NHP efficacy study demonstrated full vaccine protection against live EBOV challenge, successful inhibition of viremia, and high antibody titers following vaccination with potent titers already after two doses.

Antigen-Balancing Experiment:

An extensive mouse antigen balancing experiment has already been conducted. Swiss Webster mice (groups of 8 mice; 4M, 4F) were administered three doses (IM), 3 weeks apart of either 3 or 10 µg of each GP antigen, formulated with CoVaccine-HT™ adjuvant. The dose range selection was based on earlier mouse experiments that identified an optimal E-GP dose between 3 and 10 µg. Antibody titers (IgG) to each antigen were measured by the MIA assay for each filovirus antigen at two weeks after each dose. The results are shown in FIG. 8A, FIG. 8B.

Figure 9A:
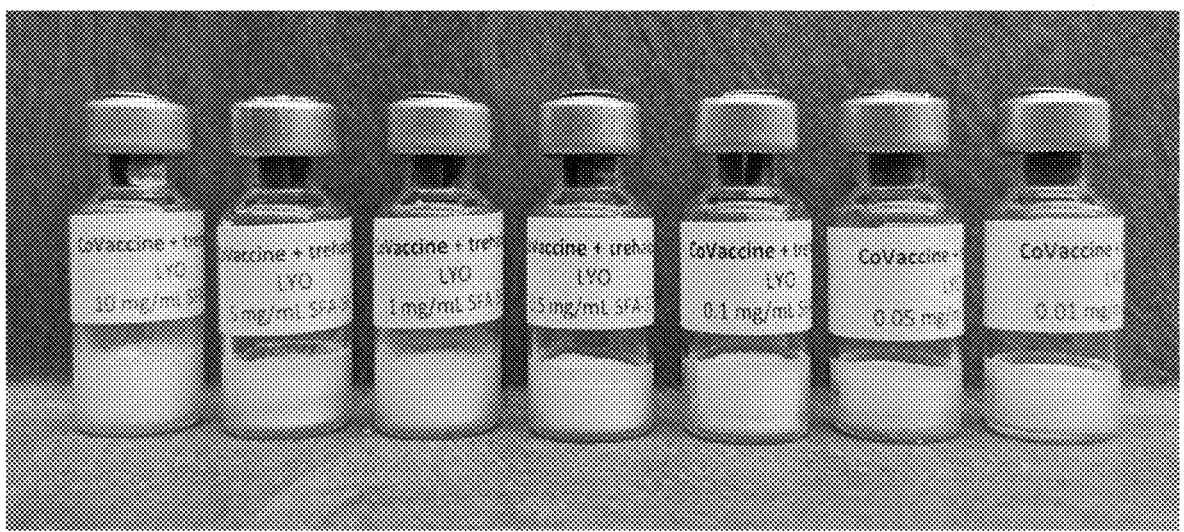
FIGS. 9A and 9B show the results of lyophilizing the Co-Vaccine-HT™ adjuvant by itself at varying concentrations in a mixture with 9.5% w/v trehalose, yielding well-formed solid cakes (9A) which can be easily reconstituted with consistent particle size (9B).
Figure 9B:
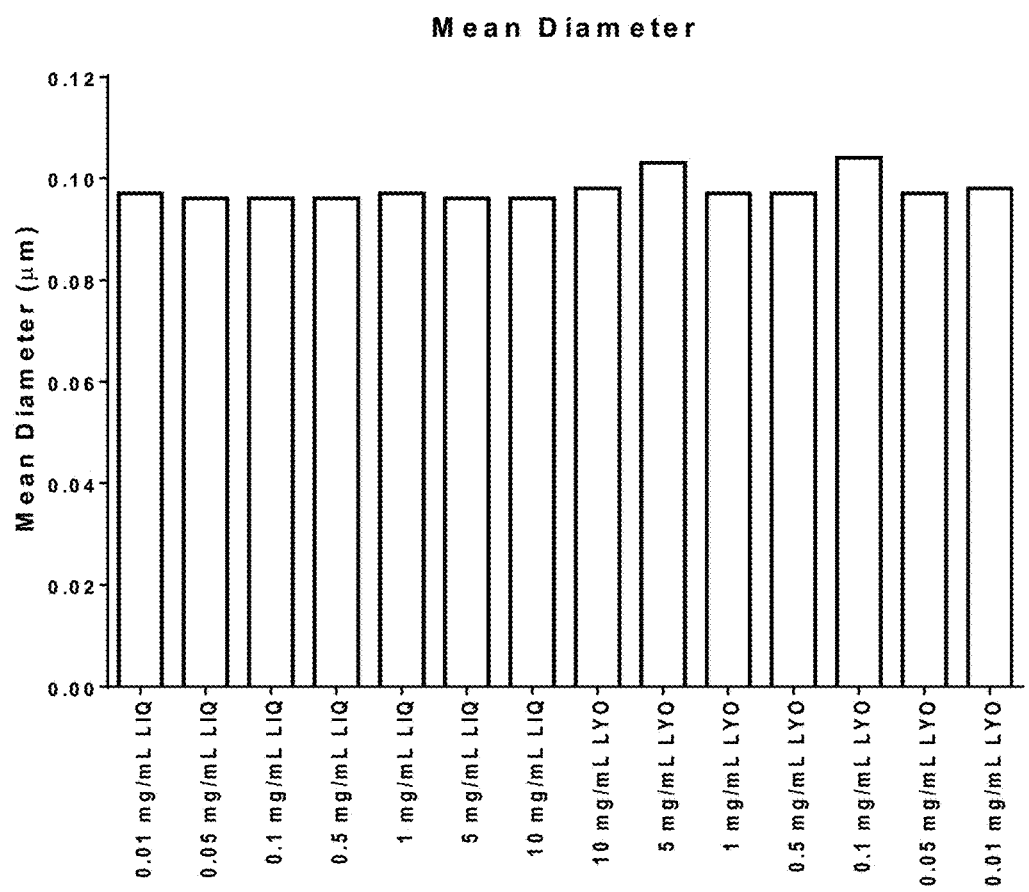

Immunogenicity of Lyophilized Adjuvant with EBOV-GP:

We conducted experiments evaluating the ability to lyophilize the adjuvant CoVaccine-HT™ under similar conditions to the GP proteins. CoVaccine-HT™ at various concentrations was mixed with 9.5% w/v trehalose and lyophilized. The resulting product showed white, well-formed cakes consistent with successful lyophilization (FIG. 9A). Moreover each vial was reconstituted with water and shown to have maintained the same particle size distribution as present prior to lyophilization (FIG. 9B).

Previous studies have shown that EBOV GP protein can be lyophilized and reconstituted while generating appropriate immune responses (Chisholm et al., Thermostable Ebola Virus Vaccine Formulations Lyophilized in the Presence of Aluminum Hydroxide. *Eur J Pharm Biopharm* 2019 March; 136:213-220). We also co-lyophilized the CoVaccine-HT™ at concentrations of 3, 5, 7 and 10 mg/ml with EBOV GP protein at concentrations of 0.01 and 0.1 mg/ml with 9.5% w/v trehalose. The resulting lyophilized compositions were tested for immunogenicity in BALB/c mice by administration on Days 0, 21 and 42 with blood draws on Day 56. The resulting blood samples revealed significant antibody titers, equivalent between the original liquid formulations and the lyophilized formulations, demonstrating the preservation of immunogenicity of the single product during the lyophilization process (FIG. 10).

Compatibility of the Formulation and Lyophilization Conditions with the MARV-GP Protein:

A study was created to determine the effects of salt, pH, and surfactant on the stability of the MARV-GP over time and temperature. Nine formulations were evaluated with varying levels of pH, salt (ammonium acetate) concentration, and surfactant (polysorbate-20) concentration. Formulations were analyzed both before and after lyophilization. A short incubation was done on lyophilized samples for 2 weeks at 50° C. to immediately evaluate immunogenicity and stability, while a longer incubation for 12 weeks at 25° C. and 40° C. was done to see the longer term stability of the formulations. The results of the study are summarized below at Table 4.

TABLE 4

MARV-GP Formulation Conditions

| Group | Salt level (ammonium acetate) | pH | Surfactant (PS-20) | Trehalose | Time points tested |
|---|---|---|---|---|---|
| 1 | 25 mM | 7 | 0 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 2 | 50 mM | 7 | 0 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 3 | 100 mM | 7 | 0 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 4 | 10 mM | 7 | 1/2x CMC = 0.03 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |

TABLE 4-continued

MARV-GP Formulation Conditions

| Group | Salt level (ammonium acetate) | pH | Surfactant (PS-20) | Trehalose | Time points tested |
|---|---|---|---|---|---|
| 5 | 10 mM | 7 | 2x CMC = 0.12 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 6 | 10 mM | 7 | 4x CMC = 0.24 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 7 | 10 mM | 5.5 | 0 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 8 | 10 mM | 6.5 | 0 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |
| 9 | 10 mM | 7.5 | 0 mg/mL | 9.5% (w/v) | LYO: 0 wk, 2 wk 50 C., 12 wk 25 C., 12 wk 40 C. LIQ: 0 wk, 12 wk 25 C., 12 wk 40 C. |

Immunogenicity testing of the samples stored for 12 weeks at 40° C. demonstrated that the formulation retained immunogenicity in BALB/c mice when dosed on Days 0, 21 and 42 with blood samples drawn for evaluation on Day 56 (FIG. 11).

Compatibility of the Formulation and Lyophilization Conditions with the SUDV-GP Protein:

A study was performed to determine the effects of salt on the stability of the SUDV-GP over time and temperature. The study is ongoing with analytical results (size exclusion chromatography) at the 8 week time point suggesting that the lyophilized formulations experienced the least amount of change (FIG. 12C) compared to the protein stored in PBS (FIG. 12A) or in the liquid formulation prior to lyophilization (FIG. 12B). The results of the study are summarized below at Table 5.

TABLE 5

SUDV-GP Formulation Conditions

| Group | Salt level (ammonium acetate) | pH | Surfactant (PS-20) | Trehalose | Time points tested |
|---|---|---|---|---|---|
| 1 | 10 mM | 7 | 0 mg/mL | 9.5% (w/v) | LYO/LIQ: 0, 4, 8 and 12 wk at 25 C. and 40 C. |
| 2 | 50 mM | 7 | 0 mg/mL | 9.5% (w/v) | LYO/LIQ: 0, 4, 8 and 12 wk at 25 C. and 40 C. |
| 3 | 100 mM | 7 | 0 mg/mL | 9.5% (w/v) | LYO/LIQ: 0, 4, 8 and 12 wk at 25 C. and 40 C. |
| 4 | 0 mM | NA | 0 mg/ml | 0 | Protein in PBS "as is": 0, 4, 8 and 12 wk at 25 C. and 40 C. |

Compatibility of the Formulation and Lyophilization Conditions with the TriValent Vaccine (EBOV-GP, MARV-GP and SUDV-GP) with and without CoVaccine-HT™ in the Same Vial:

Mixtures of all three GP subunits with and without co-lyophilized CoVaccine-HT™ have been prepared and immunogenicity assessed in rodents. Table 6 shows a comparison of the various mixtures as analyzed.

Mice were immunized intramuscularly with 100 μl (50 μl/hind leg) vaccine three times at 3-week intervals. Blood was taken two weeks after each dosing. Mice were exsanguinated at the third bleed. Antibody titers were measured on the blood by Multiplex Immunoassay using the Luminex™ system.

TABLE 6

TriValent Formulations

| ID | E-GP [μg] | S-GP [μg] | M-GP [μg] | CoV HT [mg] | Ammonium Acetate | Trehalose | pH |
|---|---|---|---|---|---|---|---|
| 1 | 0.1 | | | | 10 mM | 9.5% w/v | 7 |
| 2 | 0.3 | | | | 10 mM | 9.5% w/v | 7 |
| 3 | 1.0 | | | | 10 mM | 9.5% w/v | 7 |
| 4 | 3.0 | | | | 10 mM | 9.5% w/v | 7 |
| 5 | | 0.1 | | | 10 mM | 9.5% w/v | 7 |
| 6 | | 0.3 | | | 10 mM | 9.5% w/v | 7 |
| 7 | | 1.0 | | | 10 mM | 9.5% w/v | 7 |
| 8 | | 3.0 | | | 10 mM | 9.5% w/v | 7 |
| 9 | | | 0.1 | | 10 mM | 9.5% w/v | 7 |
| 10 | | | 0.3 | | 10 mM | 9.5% w/v | 7 |
| 11 | | | 1.0 | | 10 mM | 9.5% w/v | 7 |
| 12 | | | 3.0 | | 10 mM | 9.5% w/v | 7 |
| 13 | 0.1 | 0.1 | 0.1 | | 10 mM | 9.5% w/v | 7 |
| 14 | 0.3 | 0.3 | 0.3 | | 10 mM | 9.5% w/v | 7 |
| 15 | 1.0 | 1.0 | 1.0 | | 10 mM | 9.5% w/v | 7 |
| 16 | 3.0 | 3.0 | 3.0 | | 10 mM | 9.5% w/v | 7 |
| 17 | 0.1 | 0.04 | 0.1 | | 10 mM | 9.5% w/v | 7 |
| 18 | 0.3 | 0.12 | 0.3 | | 10 mM | 9.5% w/v | 7 |
| 19 | 1.0 | 0.4 | 1.0 | | 10 mM | 9.5% w/v | 7 |
| 20 | 3.0 | 1.2 | 3.0 | | 10 mM | 9.5% w/v | 7 |
| 21 | 0.05 | 0.05 | 0.1 | | 10 mM | 9.5% w/v | 7 |
| 22 | 0.15 | 0.15 | 0.3 | | 10 mM | 9.5% w/v | 7 |
| 23 | 0.5 | 0.5 | 1.0 | | 10 mM | 9.5% w/v | 7 |
| 24 | 1.5 | 1.5 | 3.0 | | 10 mM | 9.5% w/v | 7 |
| 25 | 0.1 | | | 0.3 | 10 mM | 9.5% w/v | 7 |
| 26 | 1.0 | | | 0.3 | 10 mM | 9.5% w/v | 7 |
| 27 | | 0.1 | | 0.3 | 10 mM | 9.5% w/v | 7 |
| 28 | | 1.0 | | 0.3 | 10 mM | 9.5% w/v | 7 |
| 29 | | | 0.1 | 0.3 | 10 mM | 9.5% w/v | 7 |
| 30 | | | 1.0 | 0.3 | 10 mM | 9.5% w/v | 7 |
| 31 | 0.1 | 0.1 | 0.1 | 0.3 | 10 mM | 9.5% w/v | 7 |
| 32 | 1.0 | 1.0 | 1.0 | 0.3 | 10 mM | 9.5% w/v | 7 |
| 33 | 0.1 | 0.04 | 0.1 | 0.3 | 10 mM | 9.5% w/v | 7 |

TABLE 6-continued

TriValent Formulations

| ID | E-GP [μg] | S-GP [μg] | M-GP [μg] | CoV HT [mg] | Ammonium Acetate | Trehalose | pH |
|---|---|---|---|---|---|---|---|
| 34 | 1.0 | 0.4 | 1.0 | 0.3 | 10 mM | 9.5% w/v | 7 |
| 35 | 0.05 | 0.05 | 0.1 | 0.3 | 10 mM | 9.5% w/v | 7 |
| 36 | 0.5 | 0.5 | 1.0 | 0.3 | 10 mM | 9.5% w/v | 7 |

Figures 13A, 13B:
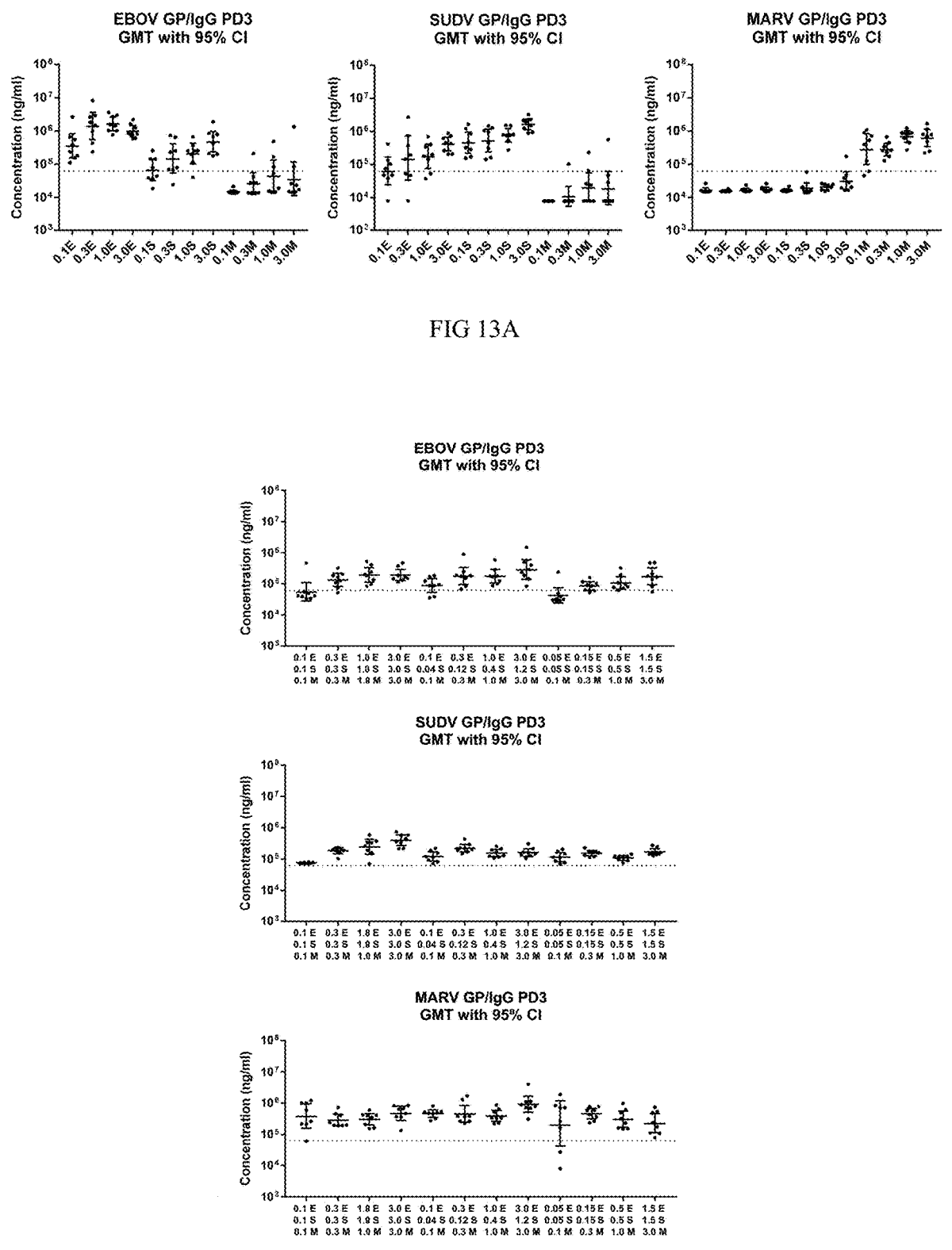
Figure 13C:
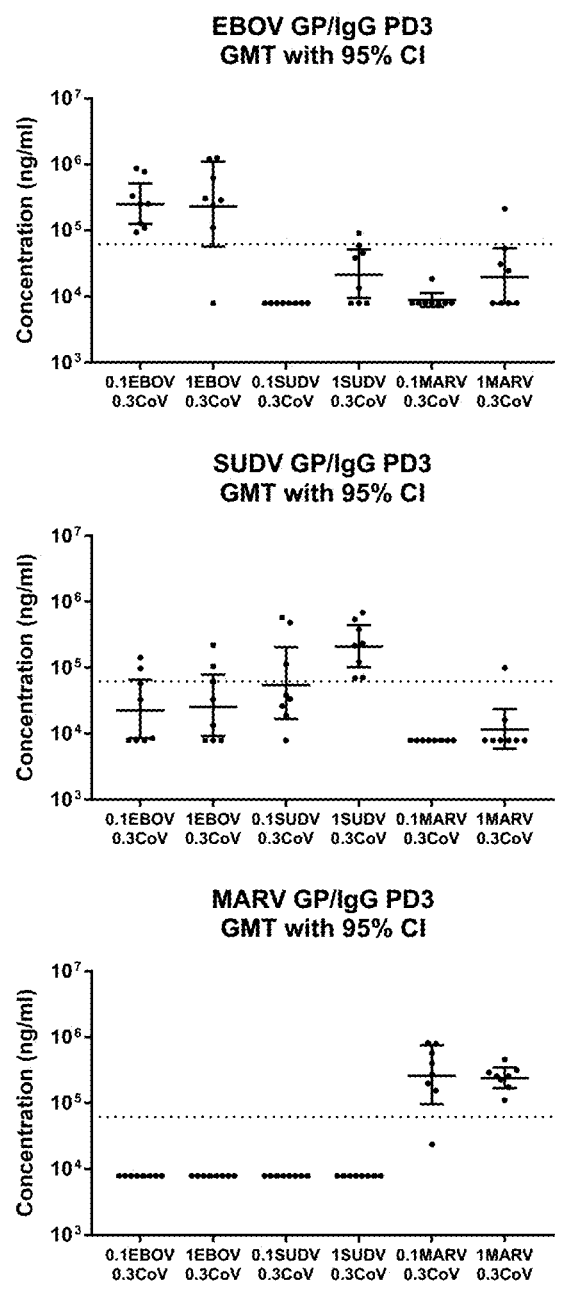
Figure 13D:
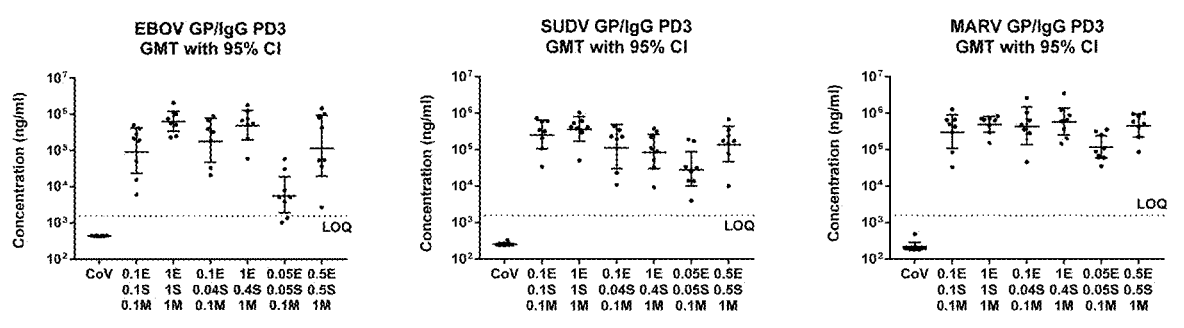

Immunogenicity was similar if CoVaccine-HT™ was co-lyophilized with the GP proteins (groups 25-36) as compared to when CoVaccine-HT™ was co-injected, but not co-lyophilized, with the GP protein mixtures (Groups 1-24), as shown in FIG. 13.

EBOV GP, MARV GP and SUDV GP are Distinct Viral Glycoproteins:

Each GP protein tested was a distinct protein species, with unique oligomerization and glycosylation. Despite these differences, each protein was compatible with the CoVaccine-HT™ adjuvant, with the selected formulation conditions and with co-lyophilization with the adjuvant under the selected formulation conditions.

Figures 14A, 14B, 14C:
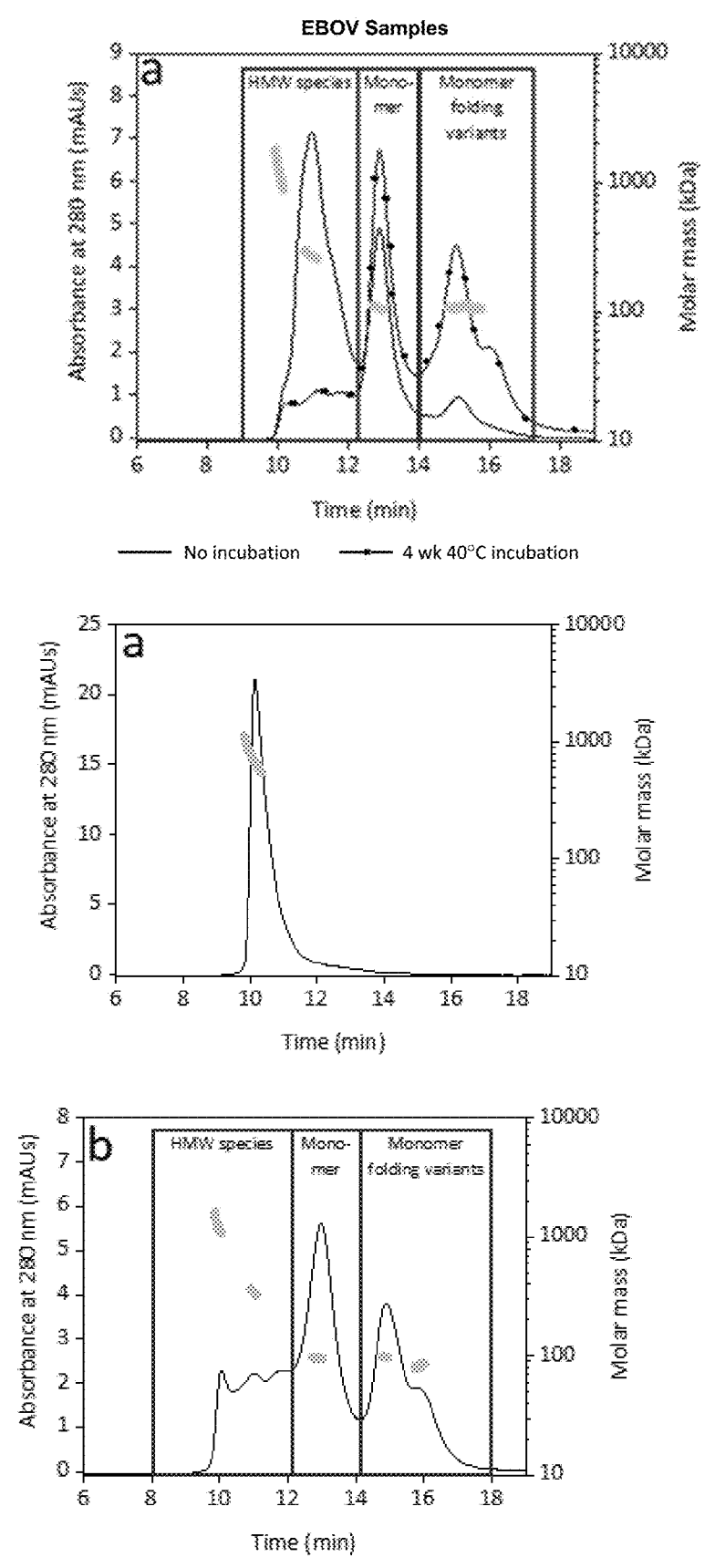

The EBOV GP protein is predominantly formed as multimers, specifically trimers and higher molecular weight species, including potentially dimers of trimers, as shown in the SEC-MALS assessment of molecular weight of the peaks identified under size exclusion chromatography (FIG. 14a). It was determined that the peak eluting at 11 minutes was an EBOV-GP trimer (with an average molecular weight of 273.1±9.5 kDa) and the peak eluting at 13 minutes was monomer (107.6±2.8 kDa). The peaks that eluted later than the monomer were determined to be folding variants of the EBOV-GP monomer because they had the same molecular weight (106.8±1.7 kDa) as the monomer but had longer retention times in size exclusion chromatography due to their increased interaction with the stationary phase. Peaks eluting earlier than 11 minutes were associated with species having molecular weights >877 kDa, and were considered to be mixtures of oligomers larger than a trimer and were therefore classified as BMW species along with the trimer peak.

The MARV GP protein is predominantly formed as a single homogenous multimer, as shown in FIG. 14b. Unlike EBOV-GP, for MARV-GP only one species was present in the chromatogram, indicating MARV-GP assembly was not prone to dissociation. This species was identified as an oligomer that was around 760 kDa.

The SUDV GP protein is also predominantly found as multimers, with a broader mix of high molecular weight aggregates as compared to EBOV GP (FIG. 14c). SUDV-GP (FIG. 7b), however, was similar to EBOV-GP in that there were multiple species present, including monomeric folding variants that have the same molecular weight as the monomer but elute at different times.

Compatibility of the Formulation and Lyophilization Conditions with a SARS-CoV-2 Vaccine (Spike Protein) with and without CoVaccine-HT' in the Same Vial:

The Spike protein of SARS-CoV-2 is a trimeric glycoprotein and will be subjected to the same formulation conditions as the other viral glycoprotein examples, as shown in Table 7. These formulations will be tested in mice and the combination, lyophilized product ("Co-Lyophilized" in Table 7) will be shown to be at least as immunogenic as the other protein formulations using the same antigen.

TABLE 7

Spike Protein Formulations

| Formulation Name | Spike protein (μg) | CoVaccine HT ™ (mg) | Excipients | Lyophilized |
|---|---|---|---|---|
| CO-Lyophilized | 25 | 0.3 | 10 mM sodium acetate 9.5% trehalose | Yes |
| Protein lyophilized* | 25 | — | 10 mM sodium acetate 9.5% trehalose | Yes |
| Protein liquid* | 25 | — | Phosphate buffered saline | No |
| CoVaccine | — | 0.3 | — | No |

*CoVaccine adjuvant will be added to a dose of 0.3 mg/mouse immediately prior to injection Each formulation will be injected into 6 Swiss Webster mice on Days 1, 21 and 42 with blood collected on days 14, 35 and 56. Anti-Sars-CoV-2 IgG titers will be determined for blood collected on Days 14, 35 and 56 and compared.

In view of the above examples, the following conclusions were drawn:

1. Full protection against EBOV in mouse, guinea pig and, most relevant, non-human primate models warranting further development of the vaccine. Our preliminary efficacy data demonstrate that the EBOV vaccine has been formulated successfully. With its demonstrated excellent safety profile (no adverse reactions observed in non-human primates) and good efficacy against high titer challenge it should be ready to advance into clinical development.
2. Surface glycoproteins (GP) have been produced and purified successfully from MARV and SUDV in addition to EBOV, and their immunogenicity and efficacy against live-virus challenge demonstrated in non-human primates. Similarly, MARV-GP and SUDV-GP are compatible with the formulation conditions identified for the EBOV-GP protein (10 mM ammonium acetate, 9.5% w/v trehalose, pH 7, lyophilized). Consequently, we believe that we have defined the basis for a filovirus vaccine effective against these three viruses.
3. Storage stability in lyophilized form of the vaccine formulation has been shown by biochemical/biophysical methods and maintenance of immunogenicity has been demonstrated in mice for EBOV-GP, MARV-GP and SUDV-GP as well as for selected mixtures of glycoproteins. It is believed that this attribute of the recombinant subunit vaccine formulation in combination with excellent stability of the selected clinical stage adjuvant allows for the development of a safe and effective trivalent filovirus vaccine that will be suitable for deployment in the field under conditions where other vaccines would encounter difficulties due to cold-chain storage requirements.
4. Lyophilization of the preferred CoVaccine-HT™ nanoemulsion adjuvant has demonstrated well-formed cakes with surprisingly well retained particulate size after reconstitution. Moreover, the combined protein and adjuvant composition co-lyophilized maintains its immunogenic profile in rodents and non-human primates, as demonstrated with EBOV-GP and MARV-GP as well as for bi- and trivalent formulations lyophilized with CoVaccine-HT™.

Laboratory Assays and Methods:

Multiplex Immunoassay (MIA): We have developed a bead-based assay in which magnetic beads (MagPix) are coated with our recombinant filovirus antigens, allowing the generation of sample- and reagent-sparing multiplex antibody assays.

Lyophilization of antigens: Vaccine formulation used in preliminary data section: 0.1 mg/mL EBOV GP, 10 mM ammonium acetate pH 7, 9.5% (w/v) trehalose±0.5 mg/mL aluminum hydroxide. Lyophilizer shelves were pre-cooled to −10° C.; shelf temperature was decreased at a rate of 0.5° C./min to −40° C. and then held at −40° C. for 1 hour. Primary drying at 60 mTorr and −20° C. for 20 hours. Secondary drying at 60 mTorr with temperature gradient to 0° C., then 30° C. followed by hold at 30° C. for 5 hours.

Size exclusion chromatography: SE-HPLC can be used to monitor the assembly state of the protein. SE-HPLC separates protein samples using two columns, a guard column and a size exclusion column. The guard column acts as a filter to remove large particles, like those greater than 1,000,000 g/mol, to protect the more sensitive HPLC column. The size exclusion column works by trapping smaller molecules in the pores of the column, so smaller molecules have longer elution times. Areas under the chromatograms (collected as light absorption at 280 nm) can be directly correlated to the mass of protein in the sample.

Size exclusion chromatography with multi-angle light scattering: To separate and then determine the molecular weights of glycoprotein species, unincubated protein samples were analyzed using SEC-MALS. SEC-MALS was performed using an ÄKTApurifier™ system (GE Healthcare Life Sciences, Marlborough, Mass.) with an in-line Wyatt Dawn Heleos II 18-angle light scattering detector (Santa Barbara, Calif.) and a Wyatt Optilab rEX refractive index detector. Samples used were stock solutions of EBOV-GP, MARV-GP, and SUDV-GP stored in PBS to allow for sufficient loading to obtain accurate molecular weights for each protein peak that eluted form the column. Before injection, samples were filtered through a 0.1 μm centrifugal filter (MilliporeSigma, Burlington, Mass.). The supernatant was passed through a TSKgel guard column and a TSKgel G3000SWXL column with the same mobile phase as used in SE-HPLC experiments. The system was operated at a flow rate of 0.5 mL/min.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted to by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A stable, immunogenic composition capable of eliciting a robust and durable immune response, comprising at least one antigen, wherein the at least one antigen comprises a viral glycoprotein, and at least one adjuvant, wherein the at least one adjuvant comprises sucrose fatty acid sulphate esters and wherein the at least one antigen and the at least one adjuvant are co-lyophilized and reconstituted immediately prior to use.

2. The composition of claim 1, wherein the composition does not include alum.

3. The composition of claim 1, wherein the composition comprises two or more antigens, wherein each antigen is specific to a different virus.

4. A method of eliciting an immune response in a mammal comprising:
   (a) providing the composition of claim 1;
   (b) reconstituting the composition of (a) prior to use with a pharmaceutically acceptable diluent; and
   (c) administering the composition to the mammal in need thereof.

5. The method of claim 4, wherein the composition is administered up to three separate occasions, resulting in the mammal being protected from subsequent infections by the virus associated with the viral glycoprotein present in the composition.

6. A stable immunogenic composition capable of eliciting a robust and durable immune response, comprising at least two antigens, wherein each antigen is a viral glycoprotein specific to a different genus of filovirus and at least one nano-emulsion adjuvant.

7. The composition of claim 6, wherein the viral glycoprotein is at least one selected from the group consisting of Marburg marburgvirus (MARV), Sudan ebolavirus (SUDV) and Zaire ebolavirus (EBOV).

8. A method of manufacturing a stable immunogenic composition capable of eliciting a robust and durable immune response to more than one virus, comprising at least two antigens, wherein each antigen is specific to a different virus from the same or different families and providing at least one adjuvant, wherein the at least one adjuvant comprises sucrose fatty acid sulphate esters and wherein the at least one antigen and the at least one adjuvant are co-lyophilized and reconstituted immediately prior to use, and further wherein the at least one adjuvant does not contain alum.

* * * * *